US009332763B2

(12) United States Patent
Di Modugno et al.

(10) Patent No.: US 9,332,763 B2
(45) Date of Patent: May 10, 2016

(54) AQUEOUS ADJUVANT CONCENTRATES WITH IMPROVED SPRAY DRIFT PROPERTIES

(71) Applicant: LAMBERTI SpA, Albizzate (IT)

(72) Inventors: Rocco Di Modugno, Giussano (IT); Filippo Quaglia, Castronno (IT); Valentina Langella, Milan (IT); Barbara Biasotti, Casarza Ligure (IT); Giovanni Floridi, Novara (IT); Giuseppe Li Bassi, Gavirate (IT)

(73) Assignee: LAMBERTI SPA, Albizzate(VA) (IT)

( * ) Notice: Subject to any disclaimer, the term of this patent is extended or adjusted under 35 U.S.C. 154(b) by 52 days.

(21) Appl. No.: 13/726,354

(22) Filed: Dec. 24, 2012

(65) Prior Publication Data

US 2013/0165322 A1 Jun. 27, 2013

(30) Foreign Application Priority Data

Dec. 23, 2011 (IT) .............................. VA11A000040

(51) Int. Cl.
*A01N 57/20* (2006.01)
*A01N 25/02* (2006.01)

(52) U.S. Cl.
CPC ................ *A01N 57/20* (2013.01); *A01N 25/02* (2013.01)

(58) Field of Classification Search
None
See application file for complete search history.

(56) References Cited

U.S. PATENT DOCUMENTS

| | | | | |
|---|---|---|---|---|
| 4,272,414 | A | | 6/1981 | Vandersall |
| 4,883,537 | A | | 11/1989 | Burdick |
| 4,971,728 | A | | 11/1990 | Vandersall |
| RE36,149 | E | | 3/1999 | Gednalske et al. |
| 5,998,072 | A | | 12/1999 | Mochizuki et al. |
| 6,322,726 | B1 | | 11/2001 | Vandersall et al. |
| 6,364,926 | B1 | * | 4/2002 | Gryzik ................. C05G 3/0064 71/34 |
| 6,479,437 | B1 | | 11/2002 | Bratz et al. |
| 6,852,674 | B2 | | 2/2005 | Bickers et al. |
| 2011/0054042 | A1 | | 3/2011 | Wu et al. |

FOREIGN PATENT DOCUMENTS

| | | | |
|---|---|---|---|
| EP | 258814 | A2 | 3/1988 |
| EP | 413274 | A2 | 2/1991 |
| EP | 510564 | A1 | 10/1992 |
| EP | 510565 | A1 | 10/1992 |
| EP | 498145 | A1 | 12/1992 |
| EP | 584227 | | 3/1994 |
| WO | 9219107 | A1 | 11/1992 |
| WO | 2010100039 | A2 | 9/2010 |

* cited by examiner

*Primary Examiner* — Robert A Wax
*Assistant Examiner* — Thor Nielsen
(74) *Attorney, Agent, or Firm* — Mossman, Kumar & Tyler PC

(57) ABSTRACT

Aqueous adjuvant concentrate with improved spray drift properties and method for its preparation comprising the steps of: i) dissolving from 15 to 30% by weight, on the weight of the final concentrate, of ammonium sulfate in water; ii) adding to the solution from 1 to 10% by weight, on the weight of the final concentrate, of anionic esters of alkyl polyglycosides; iii) dispersing in the solution from 2 to 10% by weight, on the weight of the final concentrate, of hydroxypropyl guar or hydroxypropyl guar acetate; iiii) adding ammonium sulfate to the dispersion to reach an ammonium sulfate final concentration comprised between 33 and 40% by weight.

18 Claims, 1 Drawing Sheet

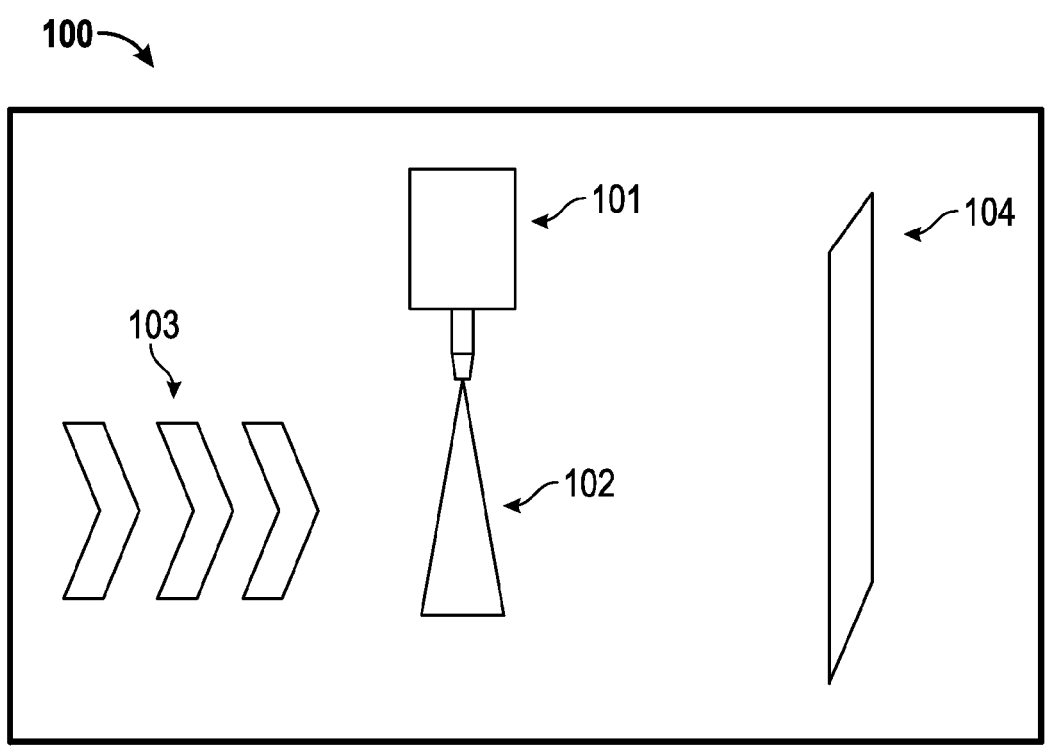

AQUEOUS ADJUVANT CONCENTRATES WITH IMPROVED SPRAY DRIFT PROPERTIES

CROSS REFERENCE TO RELATED APPLICATIONS

This application is claims priority from Italian Application Serial No. IT VA2011A000040 filed Dec. 23, 2011.

FIELD OF THE INVENTION

The invention relates to a method for the preparation of an aqueous adjuvant concentrate having improved spray drift properties comprising hydroxypropyl guar or hydroxypropyl guar acetate, ammonium sulfate and anionic esters of alkyl polyglycosides.

The invention additionally relates to the stable aqueous adjuvant concentrates prepared with the above mentioned method.

The invention further relates to stable sprayable diluted herbicidal formulations containing the above aqueous adjuvant concentrates and at least a herbicide.

BACKGROUND OF THE ART

Many known agrochemicals have shown to be more effective in combination than when applied individually.

Herbicides, and in particular glyphosate, are usually sprayed in combination with organic adjuvants (such as surfactants acting as wetting agents and stickers) and inorganic adjuvants (such as inorganic nitrogen containing fertilizers). The presence of the various adjuvants guarantees good phytoactivity and avoids detrimental and/or unpredictable effects due to local conditions (water hardness, soil quality, weather conditions, etc).

Examples of documents reporting combinations of adjuvants are U.S. Pat. No. 6,852,674, U.S. Pat. No. 6,479,437, EP 0584227, EP 498145, U.S. RE36,149 and WO 2010/100039, and the contents of the US references are fully incorporated herein by reference.

Various systems have been devised for convenient dosing of agrochemicals, such as herbicides, on field, crop area, plants etc., for example spray pumps which spray diluted agrochemical formulations (tank mix) from a opportune manifold onto the area of land or crop area, or more complex apparatus which are designed to dose concentrated agrochemical formulations into the pump and to mix them with water before being sprayed.

During the spraying of agrochemicals it is necessary to add anti-drift agents (drift control agents) in order to prevent the formation of fine droplets, which could be carried beyond the area intended to be treated. Without the use of anti-drift agents, the spraying would be largely inefficient, first of all because there could be an inadequate treatment of the land and crop areas to be treated and secondly because the extraneous spray, if carried beyond the intended treatment zone, could be detrimental to other crops, land and water courses.

Typical drift control agents are synthetic or natural polymers such as polyacrylamides, polyethylene oxides, polyvinyl pyrrolidones, guar gum and guar gum derivatives. In particular in the agriculture industry, polyacrylamides and guar gum and its derivatives are the standard additives for spray drift control.

It is usual to combine the anti-drift agent in the agrochemical formulations diluted for the spray application (tank-mix). Alternatively the anti-drift agent is dissolved in either the water which is fed into the spray pumps or applied directly into the spray pumps, usually at or shortly after the mixing zone where the water is mixed with the herbicide, pesticide or aqueous fertiliser concentrate. It is important that the spray drift chemical is correctly dosed and well dissolved to ensure that extraneous spray is not formed through under dosing or through overdosing or the spray angle is too narrow resulting in uneven distribution of the agrochemical.

However, these procedures have the problem that polymers, such as polyacrylamides, guar and guar derivatives, can be difficult to activate in field situations and polymer powders take a long time to dissolve. This can lead to the formation of gel particles which can block in-line screens and nozzles, resulting in pressure buildup in the system and spotty spray patterns.

A good solution to this problem could be dissolving/dispersing an adequate amount of anti-drift agent directly in the agrochemical concentrates. However, it is difficult to dissolve/disperse sufficient polymer in the concentrates and/or to obtain stable solutions/dispersions to achieve adequate spray drift in all cases. Furthermore, the types of polymeric antidrift agents will be limited to those which are easily soluble/dispersible in the compositions to give adequate spray drift properties.

It is well known in the art that it is possible to prepare stable suspensions/dispersions of polysaccharides in concentrated solutions of electrolytes, such as ammonium or alkali salts of sulfate, nitrate and phosphate. These suspensions/dispersions are described for example in U.S. Pat. Nos. 4,971,728, 4,272,414 and 6,322,726, which are fully incorporated herein by reference, but none of these patent describes an adjuvant composition containing also a high amount of surfactant(s).

Suspensions/dispersions of polysaccharides in solution of electrolytes and surfactants are described in U.S. Pat. Nos. 4,883,537, 5,898,072, EP 413274 and US 2011/0054042, and which US references are fully incorporated herein by reference, but these compositions require the use of suspending aids for stabilizing the suspension/dispersion. Suspending aids are usually thickeners, such as clays, fumed silica or polymeric thickening agents, or water soluble organic solvents. US 2011/0054042, for example describes compositions containing ammonium sulfate at concentration around 25-30% by weight and hydroxypropyl guar (HPG) at a concentration around 2-6% by weight and an alkyl betaine in the presence of a suspending agent, typically fumed silica, and/or a water soluble organic solvents.

U.S. Pat. No. 6,364,926, which is incorporated by reference, describes concentrated liquid adjuvant compositions comprising, by weight of the composition: a) about 25% to about 35% of a nitrogen compound in the form of an ammonium salt; b) about 0.1% to about 5% of an ampholytic surfactant, c) about 0.1% to about 2.5% of a drift control agent/deposition aid (hydroxypropyl guar), and d) about 55% to about 75% of a carrier. In this adjuvant concentrate both fertilizers and surfactants are present, but the concentration of drift control agent is quite low and does not allow high dilutions of the concentrates.

We have now discovered a specific method which allows the preparation of stable aqueous adjuvant concentrates comprising up to 10% by weight of a hydroxypropyl guar (HPG) or a hydroxypropyl guar acetate (HPGAc) as anti-drift agents, from 33 to 40% by weight of ammonium sulfate and up to 10% by weight of anionic esters of alkyl polyglycosides. These concentrates contain high amount of dissolved adjuvants, are stable, do not comprise suspending agent or a water soluble organic solvent and can be used to easily prepare in locus diluted sprayable herbicidal formulations, in particular glyphosate formulations, with optimal anti-drift characteristics.

For the purposes of this application, the terms "suspension" and "dispersion" are used interchangeably to mean a system in which solid particles (typically of HPG or HPGAc) are dispersed in a liquid (typically a salt aqueous solution).

DESCRIPTION OF THE DRAWINGS

FIG. 1. Scheme of the apparatus for the spray drift tests.

SUMMARY OF THE INVENTION

In one aspect, the invention is a method of preparing an aqueous adjuvant concentrate comprising from 33 to 40% by weight of ammonium sulfate, from 1 to 10% by weight of anionic esters of alkyl polyglycosides and from 2 to 10% by weight of hydroxypropyl guar or hydroxypropyl guar acetate comprising the steps of: i) dissolving from 15 to 30% by weight, on the weight of the final concentrate, of ammonium sulfate in water; ii) adding to the solution from 1 to 10% by weight, on the weight of the final concentrate, of anionic esters of alkyl polyglycosides; iii) dispersing in the solution from 2 to 10% by weight, on the weight of the final concentrate, of hydroxypropyl guar or hydroxypropyl guar acetate; iiii) adding ammonium sulfate to the dispersion to reach an ammonium sulfate final concentration comprised between 33 and 40% by weight.

It another aspect, the invention is a stable aqueous adjuvant concentrate comprising from 33 to 40% by weight of ammonium sulfate, from 1 to 10% by weight of anionic esters of alkyl polyglycosides and from 2 to 10% by weight of hydroxypropyl guar or hydroxypropyl guar acetate.

In still another aspect, the invention is a sprayable herbicidal formulation comprising from 0.01 to 5% by weight at least one herbicide and the above aqueous adjuvant concentrate in such an amount that the concentration of hydroxypropyl guar or hydroxypropyl acetate in the formulation is comprised between 0.05 and 0.4% by weight.

DETAILED DESCRIPTION OF THE INVENTION

Ammonium sulfate and the surfactant, and optionally other additives, can be dissolved in water utilizing common equipment. The same equipment can be used for suspending the guar derivatives in the obtained salt solution and lastly the rest of the ammonium sulfate. No special or particular equipment is required for the preparation of the aqueous adjuvant concentrate of the application.

The aqueous adjuvant concentrate is stable; with the term "stable" it is meant that no phase separation or precipitation or gelification occur, also in difficult environmental conditions, such as high (>40° C.) or low (<10° C.) temperatures for at least one week from its preparation.

The stability of the suspension can be further improved by mixing the dispersion under vacuum, so as to remove entrapped air.

Typically the aqueous adjuvant concentrate comprises at least 35% by weight, preferably from 40 to 60% by weight, of water. In some embodiments, the water is added in a single portion in the step.

The anionic esters of alkyl polyglycosides useful with the application may be compounds represented by the general formula (I) $[R—O-(G)_x]_n-(D)_y$, where R is an aliphatic alkyl group, saturated or unsaturated, linear or branched, having from 6 to 20 atoms of carbon, preferably from 8 to 16 carbon atoms; G is a residue of a reducing saccharide, preferably of glucose, connected to R—O by means of an ethereal O-glycosidical bond; O is an oxygen atom; D is an acyl residue connected to an oxygen atom of the residue G, and derived from a dicarboxylic acid or a polycarboxylic acid having an aliphatic chain from 2 to 8 carbon atoms, linear or branched, saturated or unsaturated, not substituted or substituted with one or more hydroxyl groups or a sulfonate group, and in which at least one carboxylic group is salified or in acid form; n is a number between 1 and m-1, where m is the number of carboxylic groups in the acid that originates D; x is a number from 1 to 10, representing the average degree of oligomerization of G; y is a number from 1 to 10 representing the medium degree of esterification. The above mentioned anionic esters of alkyl polyglycosides of formula (I) are known and they can be prepared as described, for example, in EP 258 814, EP 510 564 or EP 510 565.

In one embodiment of the application, in formula (I) R is an aliphatic alkyl group, saturated or unsaturated, linear or branched, having from 8 to 16 carbon atoms, G is glucose, x is between 1.0 and 2.5 and D is the acyl residue of a carboxylic acid selected from the group consisting of citric acid, tartaric acid, maleic acid, malic acid and sulfosuccinic acid.

Anionic esters of alkyl polyglucosides of formula (I) in which R is an alkyl group having from 8 to 16 atoms of carbon, G is glucose, x is between 1.0 and 2.5 and D is the acyl residue of citric acid (citric esters of $C_8$-$C_{16}$ alkyl polyglucosides) gave the best results in terms of the composition stability.

The hydroxypropyl guar or hydroxypropyl guar acetate suitable as anti-drift agents in the practice of the method of the application can be prepared by using any of the procedures well known to those of ordinary skill in the art.

"Guar gum" or simply "guar" is a galactomannan obtained by the thermo-mechanical treatment of the seeds of "*Cyamopsis Tetragonolobus*", a leguminosae cultivated in the semi-dry region of tropical countries, particularly in India and in Pakistan.

Hydroxypropyl derivatives of guar are obtained by chemical reaction of the hydroxyl groups of the galactomannan chain with propylene oxide, in the presence of an alkaline catalyst (such as sodium hydroxide). In the known processes for the production of hydroxypropyl guar, such reaction is carried out in a water-solvent media wherein the solvent is typically an alcohol, as described, for example, in U.S. Pat. Nos. 3,326,890, 3,723,409 etc.

For the preparation of the acetate derivative, before or after the hydroxypropylation, an acetylating agent can be introduced in the alkaline reaction mixture. This acetylating agent can be, for example, acetic anhydride, acetyl chloride or acetic acid.

All hydroxypropyl guar (acetate) commonly used in the field can be dispersed in the aqueous adjuvant concentrate of the compositions of the application. The commercially available HPG roughly belong to two categories: crude products, that is, products still containing by-products generated during their chemical preparation (glycols, polyglycols, inorganic/organic salts) and purified products. Purified hydroxypropyl guar possess a higher percentage of active substance than the crude product and obviously exhibits better thickening and rheological characteristics.

For this reason, after the neutralization, the HPG or the HPGAc of the disclosure may be purified by washing with water, an organic solvent, or a mixture of both usually in the presence of a crosslinking agent such as boric acid or its salts, or glyoxal.

At the end of the process the guar derivatives are usually dried and recovered using means known in the art.

In one desirable embodiment the HPG has molar hydroxypropyl substitution from 0.1 to 3.0, preferably from 0.2 to 1.3 and more preferably from 0.2 to 0.7. The expression "molar hydroxypropyl substitution" (MS) means the average number of moles of hydroxypropyl groups for each anhydroglycosidic unit of the guar and can be measured by $^1$H-NMR.

In another preferred embodiment the hydroxypropyl guar acetate has a molar hydroxypropyl substitution from 0.1 to 1.0 and contains an average of from 0.001 to 0.15 preferably from 0.005 to 0.05, of acetate groups per anhydroglycosidic unit (DS).

The HPG or HPGAc useful with the application have Brookfield® RVT viscosity at 20° C., 20 rpm and 1% in water comprised between 500 and 10,000 mPa·s, preferably between 1,000 and 5,000 mPa·s.

In another embodiment the anti-drift agent is a glyoxalated hydroxypropyl guar with a MS comprised between 0.2 and 0.7 and a Brookfield® RVT viscosity at 20° C., 20 rpm, 1% in water of from 1500 to 3500 mPa·s.

Other nitrogenous fertilizers can be present in the composition of the disclosure.

Examples of suitable fertilizers are aqueous ammonia solutions, ammonium nitrate, ammonium hydrogen sulfate, ammonium chloride, ammonium acetate, ammonium formate, ammonium oxalate, ammonium carbonate, ammonium hydrogen carbonate, ammonium thiosulfate, ammonium phosphate, diammonium hydrogen phosphate, ammonium dihydrogen monophosphate, ammonium sodium hydrogen phosphate, ammonium thiocyanate, urea and thiourea, and mixtures of these, and also ammonium nitrate/urea solutions (UAN or AHL solutions). These fertilizers are preferably added in step iiii) after the HPG/HPGAc.

Optionally, the adjuvant concentrate may also include humectants, corrosion inhibitors, microbial inhibitors, pH adjusters, anti-foam agents or mixture thereof. These further additives may be added at any time, but they are preferably added after the ammonium sulfate and before the HPG/HPGAc.

The aqueous adjuvant concentrates of the disclosure are pourable, stable, and can be stored for a long time without a settling or precipitation of solid components from the composition, despite the large amount of ammonium sulfate and surfactants that they contain; advantageously, they do not comprise any suspending agent or water soluble organic solvent, except the hydroxypropyl guar or hydroxypropyl guar acetate.

The sprayable herbicide formulations are diluted and are obtained by adding the adjuvant concentrates to formulated herbicides, or vice versa, and possibly diluting with water to the desired concentration in order to obtain aqueous formulation which can be directly sprayed on the fields.

Alternatively, the formulated herbicide and/or the adjuvant concentrates may be previously diluted and then mixed.

The term "diluted" is used herein with reference to herbicide active content comprised between 0.001 and 5% by weight.

Said sprayable herbicide formulations comprise herbicidal active compounds, such as Acetochlor, Acibenzolar, Acibenzolar-S-methyl, Acifluorfen, Acifluorfen-sodium, Aclonifen, Alachlor, Allidochlor, Alloxydinn, Alloxydinn-sodium, Ametryn, Amicarbazone, Amidochlor, Amidosulfuron, Aminocyclopyrachlor, Aminopyralid, Amitrole, Ammonium sulfamat, Ancymidol, Anilofos, Asulam, Atrazine, Azafenidin, Azimsulfuron, Aziprotryn, Beflubutamid, Benazolin, Benazolin-ethyl, Bencarbazone, Benfluralin, Benfuresate, Bensulide, Bensulfuron, Bensulfuron-methyl, Bentazone, Benzfendizone, Benzobicyclon, Benzofenap, Benzofluor, Benzoylprop, Bicyclopyrone, Bifenox, Bispyribac, Bispyribac-sodium, Bromacil, Bromobutide, Bromofenoxim, Bromoxynil, Bromuron, Buminafos, Busoxinone, Butachlor, Butafenacil, Butamifos, Butenachlor, Butralin, Butroxydim, Butylate, Cafenstrole, Carbetamide, Carfentrazone, Carfentrazone-ethyl, Chlomethoxyfen, Chloramben, Chlorazifop, Chlorazifop-butyl, Chlorbromuron, Chlorbufam, Chlorfenac, Chlorfenac-sodium, Chlorfenprop, Chlorflurenol, Chlorflurenol-methyl, Chloridazon, Chlorimuron, Chlorimuron-ethyl, Chlormequat-chloride, Chlornitrofen, Chlorophthalim, Chlorthal-dimethyl, Chlorotoluron, Chlorsulfuron, Cinidon, Cinidon-ethyl, Cinmethylin, Cinosulfuron, Clethodim (C10), Clodinafop, Clodinafop-propargyl, Clofencet, Clomazone, Clomeprop, Cloprop, Clopyralid (C1), Cloransulam, Cloransulam-methyl, Cumyluron, Cyanamide, Cyanazine, Cyclanilide, Cycloate, Cyclosulfamuron, Cycloxydim (C11), Cycluron, Cyhalofop, Cyhalofop-butyl, Cyperquat, Cyprazine, Cyprazole, 2,4-D, 2,4-DB, Dalapon, Daminozide, Dazomet, n-Decanol, Desmedipham, Desmetryn, Detosyl-Pyrazolate (DTP), Diallate, Dicamba, Dichlobenil, Dichlorprop, Dichlorprop-P, Diclofop, Diclofop-methyl, Diclofop-P-methyl, Diclosulam, Diethatyl, Diethatyl-ethyl, Difenoxuron, Difenzoquat, Diflufenican, Diflufenzopyr, Diflufenzopyr-sodium, Dimefuron, Dikegulac-sodium, Dimefuron, Dimepiperate, Dimethachlor (C2), Dimethametryn, Dimethenamid, Dimethenamid-P, Dimethipin, Dimetrasulfuron, Dinitramine, Dinoseb, Dinoterb, Diphenamid, Dipropetryn, Diquat, Diquat-dibromide, Dithiopyr, Diuron, DNOC, Eglinazine-ethyl, Endothal, EPTC, Esprocarb, Ethalfluralin, Ethametsulfuron, Ethametsulfuron-methyl, Ethephon, Ethidimuron, Ethiozin, Ethofumesate, Ethoxyfen, Ethoxyfen-ethyl, Ethoxysulfuron, Etobenzanid, F-5331, d.h. N-[2-Chloro-4-fluoro-5-[4-(3-fluoropropyl)-4,5-dihydro-5-oxo-1H-tetrazol-1-yl]-phenyl]-ethan sulfonamide, F-7967, d.h. 3-[7-Chloro-5-fluoro-2-(trifluoromethyl)-1H-benzimidazol-4-yl]-1-methyl-6-(trifluormethyl) pyrimidin-2,4(1H,3H)-dione, Fenoprop, Fenoxaprop, Fenoxaprop-P, Fenoxaprop-ethyl, Fenoxaprop-P-ethyl (C3), Fenoxasulfone, Fentrazamide, Fenuron, Flamprop, Flamprop-M-isopropyl, Flamprop-M-methyl, Flazasulfuron, Florasulam, Fluazifop, Fluazifop-P, Fluazifop-butyl, Fluazifop-P-butyl, Fluazolate, Flucarbazone, Flucarbazone-sodium, Flucetosulfuron, Fluchloralin, Flufenacet (Thiafluamide), Flufenpyr, Flufenpyr-ethyl, Flumetralin, Flumetsulam, Flumiclorac, Flumiclorac-pentyl, Flumioxazin, Flumipropyn, Fluometuron, Fluorodifen, Fluoroglycofen, Fluoroglycofen-ethyl, Flupoxam, Flupropacil, Flupropanate, Flupyrsulfuron, Flupyrsulfuron-methyl-sodium, Flurenol, Flurenol-butyl, Fluridone, Fluorochloridone, Fluoroxypyr, Fluoroxypyr-meptyl, Flurprimidol, Flurtamone, Fluthiacet, Fluthiacet-methyl, Fluthiamide, Fomesafen, Foramsulfuron, Forchlorfenuron, Fosamine, Furyloxyfen, Glufosinate, Glufosinate ammonium, Glyphosate, Glyphosate-diammonium, Glyphosate-isopropylammonium, Glyphosate-potassium, H-9201, d.h. O-(2,4-Dimethyl-6-nitrophenyl)-O-ethyl-isopropyl phosphoramidothioate, Halosafen, Halosulfuron, Halosulfuron-methyl, Haloxyfop, Haloxyfop-p (C4), Haloxyfop-ethoxyethyl, Haloxyfop-P-ethoxyethyl, Haloxyfop-methyl, Haloxyfop-P-methyl, Hexazinone, HW-02, d.h. 1-(Dimethoxyphosphoryl)-ethyl(2,4-dichlorophenoxy)acetate, Imazamethabenz, Imazamethabenz-methyl, Imazamox (C9), Imazamox-ammonium, Imazapic, Imazapyr, Imazapyr-isopropylammonium, Imazaquin, Imazaquin-ammonium, Imazethapyr, Imazethapyr-ammonium, Imazosulfuron, Inabenfide, Indanofan, Indaziflam, Indolacetic acid (IAA), 4-Indol-3-yl-butirric acid (IBA), Iodosulfuron, Iodosulfuron-methyl-sodium, Ioxynil, Ipfencarbazone, Isocarbamid, Isopropalin, Isoproturon, Isouron, Isoxaben, Isoxachlortole, Isoxaflutole, Isoxapyrifop, KUH-043, d.h. 3-({[5-(Difluoromethyl)-1-methyl-3-(trifluoromethyl)-1H-pyrazol-4-yl]methyl}sulfonyl)-5,5-dimethyl-4,5-dihydro 1,2-oxazole, Karbutilate, Ketospiradox, Lactofen, Lenacil, Linuron, MCPA, MCPB, MCPB-methyl, -ethyl and -sodium, Mecoprop, Mecoprop-sodium, Mecoprop-butotyl, Mecoprop-P-butotyl, Mecoprop-P-dimethylammoniunn, Mecoprop-P-2-ethylhexyl, Mecoprop-P-potassium, Mefenacet, Mefluidide, Mepiquat-chlorid, Mesosulfuron, Mesosulfuron-methyl, Mesosulfuron-methyl-Na, Mesotrione, Methabenzthiazuron, Metam, Metamifop, Metamitron, Metazachlor (C5), Metazasulfuron, Methazole, Methiopyrsulfuron, Methiozolin, Methoxyphenone, Methyldymron, 1-Methylcyclopropen, Methylisothiocyanat, Metobenzuron, Metobromuron, Metolachlor, S-Metolachlor, Metosulam, Metoxuron, Metribuzin, Metsulfuron, Metsulfuron-methyl, Molinate, Monalide, Monocarbamide, Monocarbamide-dihydrogensulfat, Monolinuron, Monosulfuron, Monosulfuron-ester, Monuron, MT-128, d.h. 6-Chloro-N-[(2E)-3-chloroprop-2-en-1-yl]-5-methyl-N-phenylpyridazin-3-amine, MT-5950, d.h. N-[3-Chloro-4-(1-methylethyl)-phenyl]-2-methylpentanamide, NGGC-011, Naproanilide, Napropamide (C6), Naptalam, NC-310, d.h. 4-(2,4-Dichlorobenzoyl)-1-methyl-5-benzyloxypyrazole, Neburon, Nicosulfuron, Nipyraclofen, Nitralin, Nitrofen, Nitrophenolat-sodium (isomer mixture), Nitrofluorfen, Nonansäure, Norflurazon, Orbencarb, Orthosulfamuron, Oryzalin, Oxadiargyl, Oxadiazon, Oxasulfuron, Oxaziclomefone, Oxyfluorfen, Paclobutrazol, Paraquat, Paraquat-dichlorid, Pendimethalin, Pendralin, Penoxsulam, Pentanochlor, Pentoxazone, Perfluidone, Pethoxamid, Phenisopham, Phenmedipham, Phenmedipham-ethyl, Picloram, Picolinafen, Pinoxaden, Piperophos, Pirifenop, Pirifenop-butyl, Pretilachlor, Primisulfuron, Primisulfuron-methyl, Probenazole, Profluazol, Procyazine, Prodiamine, Prifluraline, Profoxydim, Prohexadione, Prohexadione-calcium, Prohydrojasmone, Prometon, Prometryn, Propachlor, Propanil, Propaquizafop, Propazine, Propham, Propisochlor, Propoxycarbazone, Propoxycarbazone-sodium, Propyrisulfuron, Propyzamide, Prosulfalin, Prosulfocarb, Prosulfuron, Prynachlor, Pyraclonil, Pyraflufen, Pyraflufen-ethyl, Pyrasulfotole, Pyrazolynate (Pyrazolate), Pyrazosulfuron, Pyrazosulfuron-ethyl, Pyrazoxyfen, Pyribambenz, Pyribambenz-isopropyl, Pyribambenz-propyl, Pyribenzoxim, Pyributicarb, Pyridafol, Pyridate (C7), Pyriftalid, Pyriminobac, Pyriminobac-methyl, Pyrimisulfan, Pyrithiobac, Pyrithiobac-sodium, Pyroxasulfone, Pyroxsulam, Quinclorac, Quinmerac, Quinoclamine, Quizalofop, Quizalofop-ethyl, Quizalofop-P, Quizalofop-P-ethyl, Quizalofop-P-tefuryl, Rimsulfuron, Saflufenacil, Secbumeton, Sethoxydim, Siduron, Simazine, Simetryn, SN-106279, d.h. Methyl-(2R)-2-({7-[2-chloro-4-(trifluoromethyl)phenoxy]-2-naphthyl}oxy) propanoate, Sulcotrione, Sulfallate (CDEC), Sulfentrazone, Sulformeturon, Sulformeturon-methyl, Sulfosate (Glyphosate-trimesium), Sulfosulfuron, SYN-523, SYP-249, d.h. 1-Ethoxy-3-methyl-1-oxobut-3-en-2-yl-5-[2-chloro-4-(trifluoromethyl)phenoxy]-2-nitrobenzoate, SYP-300, d.h. 1-[7-Fluoro-3-oxo-4-(prop-2-in-1-yl)-3,4-dihydro-2H-1,4-benzoxazin-6-yl]-3 propyl-2-thioxoimidazolidin-4,5-dione, Tebutam, Tebuthiuron, Tecnazene, Tefuryltrione, Tembotrione, Tepraloxydim, Terbacil, Terbucarb, Terbuchlor, Terbumeton, Terbuthylazine, Terbutryn, Thenylchlor, Thiafluamide, Thiazafluoron, Thiazopyr, Thidiazimin, Thidiazuron, Thiencarbazone, Thiencarbazone-methyl, Thifensulfuron, Thifensulfuron-methyl, Thiobencarb, Tiocarbazil, Topramezone, Tralkoxydim, Triallate, Triasulfuron, Triaziflam, Triazofenamide, Tribenuron, Tribenuron-methyl, Trichloroacetic acid (TCA), Triclopyr, Tridiphane, Trietazine, Trifloxysulfuron, Trifloxysulfuron-sodium, Trifluralin (C8), Triflusulfuron, Triflusulfuron-methyl, Trimeturon, Trinexapac, Trinexapac-ethyl, Tritosulfuron, Tsitodef, Uniconazole, Uniconazole-P, Vernolate, ZJ-0862, d.h. 3,4-Dichloro-N-{2-[(4,6-dimethoxypyrimidin-2-yl)oxy]benzyl}aniline or mixture thereof.

The adjuvant concentrates are particularly suited for the preparation of sprayable formulations of N-(phosphonomethyl)glycine (Glyphosate) and its salts, and preferably for the isopropylammonium salt of N-(phosphonomethyl)glycine (Glyphosate isopropylammonium).

Other biologically active ingredients such as other pesticides, plant growth regulators, algicides, fungicides, bactericides, viricides, insecticides, acaricides and nematicides may be added as partners in the sprayable diluted herbicide formulations.

The sprayable herbicidal formulations may additionally comprise other conventional additives, including thickeners, flow enhancers, wetting agents, buffers, lubricants, fillers, deposition enhancers, evaporation retardants, frost protecting agents, insect attracting odor agents, UV protecting agents, fragrances, anti-foam agents and the like. Notwithstanding this, the compositions of the application are prepared in the substantial absence of pinolene compounds.

Application rates will depend upon the weeds to be controlled and the degree of control desired. In general, the herbicidal formulations useful with the methods of the disclosure are most efficiently employed at a rate of 0.001 to 22.4 kilograms per hectare of the active ingredients, preferably 0.01 to 16.8 kilograms per hectare.

Thanks to the presence of the anionic esters of alkyl polyglycosides, the ammonium sulfate does not precipitate out of the composition when other materials, such as the herbicide, are added and, at the same time, the biological activity of the herbicide is further increased.

The sprayable diluted herbicidal formulations may give optimum drift control and droplet deposition, and have also high storage stability and do not tend to block the spray nozzles.

The following Examples serve to illustrate the stability of aqueous adjuvant concentrate of the disclosure.

EXAMPLES

Example 1-31

Different amounts of ammonium sulfate (AMS 1, see Tables 1-5) were dissolved in deionized water at room temperature under stirring.

After complete solubilization DEFOMEX 2033 N, an antifoaming agent, and Emulson AGE/EC/UP, an alkyl polyglucoside citrate, both commercialized by Lamberti S.p.A., were added.

The mixture was maintained under mechanical stirring until complete dissolution, then glyoxylated hydroxypropyl guar (HPG1, MS 0.3 and a Brookfield® RVT viscosity of 2500 mPa·s at 1% water sol., 20° C. and 20 rpm) or hydroxypropyl guar acetate (HPGAc1, MS (hydroxypropyl) 0.4, DS (acetate) 0.015 and Brookfield® RVT viscosity of 2270 mPa·s, at 1% water sol., 20° C. and 20 rpm) were added.

The preparation of the concentrates and of the comparative Examples 12, 17, 18 and 25 was completed with the final addition, in small portion, of other ammonium sulfate (AMS 2).

Tables 1-5 report the amount in grams of the ingredients utilized and the appearance and the stability at different temperature of the final dispersions.

TABLE 1

| Ingredient | Example 1* | Example 2* | Example 3 | Example 4 | Example 5* | Example 6 |
|---|---|---|---|---|---|---|
| Deionized Water | 54.0 | 54.0 | 54.0 | 54.0 | 46 | 52 |
| AMS 1 | 15.0 | 34.0 | 30.0 | 25.0 | 40 | 30 |
| DEFOMEX 2033 N | 1.0 | 1.0 | 1.0. | 1.0. | 1 | 1 |
| EMULSON AGE/EC/UP | 6.0 | 6.0 | 6.0 | 6.0 | 6 | 6 |
| HPG1 | 5.0 | 5.0 | 5.0 | 5.0 | 7 | 7 |
| AMS 2 | — | — | 4.0 | 9.0 | — | 4 |
| Appearance | Too Viscous | Phase Separ. | Homog. Dispers. | Homog. Dispers. | Phase Separ. | Homog. Dispers. |
| Stability 54° C. 15 days | n.d. | n.d. | Stable | Stable | n.d. | Stable |
| Stability 4° C. 7 days | n.d. | n.d. | Stable | Stable | n.d. | Stable |

*comparative n.d. not determined

Phase Separ. = phase separation occurred

Homog. Dispers. = homogeneous dispersion

TABLE 2

| Ingredient | Example 7 | Example 8 | Example 9 | Example 10 | Example 11 | Example 12* |
|---|---|---|---|---|---|---|
| Deionized Water | 46 | 52 | 52 | 46 | 46 | 46 |
| AMS 1 | 30 | 25 | 20 | 20 | 15 | 10 |
| Defomex 2033 N | 1 | 1 | 1 | 1 | 1 | 1 |
| Eucarol AGE/EC/UP | 6 | 6 | 6 | 6 | 6 | 6 |
| HPG1 | 7 | 7 | 7 | 7 | 7 | 7 |
| AMS 2 | 10 | 9 | 14 | 20 | 25 | 30 |
| Appearance | Homog. Dispers. | Homog. Dispers. | Homog. Dispers. | Homog. Dispers. | Homog. Dispers. | Too Viscous |
| Stability 54° C. 15 days | Stable | Stable | Stable | Stable | Stable | n.d. |
| Stability 4° C. 7 days | Stable | Stable | Stable | Stable | Stable | n.d. |

*comparative n.d. not determined

Phase Separ. = phase separation occurred

Homog. Dispers. = homogeneous dispersion

TABLE 3

| Ingredient | Example 13* | Example 14* | Example 15 | Example 16 | Example 17* | Example 18* |
|---|---|---|---|---|---|---|
| Deionized Water | 50 | 56 | 56 | 50 | 56 | 50 |
| AMS 1 | 40 | 34 | 20 | 15 | 10 | 10 |
| Defomex 2033 N | 1 | 1 | 1 | 1 | 1 | 1 |
| Eucarol AGE/EC/UP | 6 | 6 | 6 | 6 | 6 | 6 |
| HPG1 | 3 | 3 | 3 | 3 | 3 | 3 |
| AMS 2 | — | — | 14 | 25 | 24 | 30 |
| Appearance | Phase Separ. | Phase Separ. | Homog. Dispers. | Homog. Dispers. | Phase Separ. | Too Viscous |
| Stability 54° C. 15 days | n.d. | n.d. | Stable | Stable | n.d. | n.d. |
| Stability 4° C. 7 days | n.d. | n.d. | Stable | Stable | n.d. | n.d. |

*comparative n.d. not determined

Phase Separ. = phase separation occurred

Homog. Dispers. = homogeneous dispersion

TABLE 4

| Ingredient | Example 19* | Example 20 | Example 21 | Example 22 | Example 23 | Example 24 | Example 25* |
|---|---|---|---|---|---|---|---|
| Deionized Water | 46 | 46 | 46 | 52 | 46 | 46 | 46 |
| AMS 1 | 40 | 34 | 30 | 25 | 20 | 15 | 10 |
| Defomex 2033 N | 1 | 1 | 1 | 1 | 1 | 1 | 1 |
| Eucarol AGE/EC/UP | 6 | 6 | 6 | 6 | 6 | 6 | 6 |
| HPGAc | 7 | 7 | 7 | 7 | 7 | 7 | 7 |
| AMS 2 | | 6 | 10 | 9 | 20 | 25 | 30 |

TABLE 4-continued

| Ingredient | Example 19* | Example 20 | Example 21 | Example 22 | Example 23 | Example 24 | Example 25* |
|---|---|---|---|---|---|---|---|
| Appearance | Phase Separ. | Phase Separ. | Homog. Dispers. | Homog. Dispers. | Homog. Dispers. | Homog. Dispers. | Too Viscous |
| Stability 54° C. 15 days | n.d. | n.d. | Stable | Stable | Stable | Stable | n.d. |
| Stability 4° C. 7 days | n.d. | n.d. | Stable | Stable | Stable | Stable | n.d. |

*comparative
n.d. not determined
Phase Separ. = phase separation occurred
Homog. Dispers. = homogeneous dispersion

TABLE 5

| Ingredient | Example 26* | Example 27* | Example 28 | Example 29 | Example 30 | Example 31 |
|---|---|---|---|---|---|---|
| Deionized Water | 50 | 55 | 56 | 50 | 56 | 50 |
| AMS 1 | 40 | 35 | 20 | 20 | 15 | 15 |
| Defomex 2033 N | 1 | 1 | 1 | 1 | 1 | 1 |
| Eucarol AGE/EC/UP | 6 | 6 | 6 | 6 | 6 | 6 |
| HPGAc | 3 | 3 | 3 | 3 | 3 | 3 |
| AMS 2 | — | — | 14 | 20 | 19 | 25 |
| Appearance | Phase Separ. | Phase Separ. | Homog. Dispers. | Homog. Dispers. | Homog. Dispers. | Homog. Dispers. |
| Stability 54° C. 15 days | n.d. | n.d. | Stable | Stable | Stable | Stable |
| Stability 4° C. 7 days | n.d. | n.d. | Stable | Stable | Stable | Stable |

*comparative
n.d. not determined
Phase Separ. = phase separation occurred
Homog. Dispers. = homogeneous dispersion The aqueous adjuvant concentrates (dispersions) are considered stable when no phase separation or precipitation or gelification occur.

Every dispersion prepared with the method of the disclosure was homogeneous. The dispersions prepared with a high initial concentration of ammonium sulfate (Examples 1, 2, 13, 14, 19, 20, 26 and 27) gave an almost immediate phase separation, those prepared (Examples 12, 18 and 25) with a low initial concentration, became too viscous to be handled.

Spray Drift Test

The spray drift properties were tested by diluting the aqueous adjuvant concentrates of Examples 3 and 28 to a final concentration of HPG or HPGAc of 0.2 and 0.3% by weight in CIPAC D water containing 1% by weight of a composition that simulates a Glyphosate based SL formulation containing:
1
0% by weight Tallow amine ethoxylated (15EO)
9
0% by weight water buffered at pH 4.7.

CIPAC D water containing 1% of the composition simulating Glyphosate based SL formulation was used as the blank solution (comparative).

The anti-drift effect was evaluated in a wind chamber (see FIG. 1) at a temperature of 22° C.±2.

The diluted herbicide spray formulation was pumped at a pressure of 2.0 bar through a Teejet TP 11003 VP nozzle, placed vertically at 60 cm from the floor. An axial fan pulled air through the wind chamber colliding transversally the spray cone at a speed of approximately 4 m/s.

Each sample was sprayed for 40 seconds.

Drifted droplets were collected by a weighted dry paper sheet (W×L×H=0.8 m×0.8 m×0.2 cm), placed upright, 90 cm ahead of the spray cone opposite to the fan. Drift was determined as weight difference measured before and after 1 minute from the collection.

All tests were replicated 3 times.

The drift % (mean value) is reported in Table 6 as percentage considering 100% the drift of the blank (spray formulation without anti drift agent).

TABLE 6

| | HPG/HPGAc | Drift % | Drift % Reduction |
|---|---|---|---|
| Blank* | — | 100 | 0 |
| Example 28 | 0.20% | 12.2 | 87.8 |
| Example 28 | 0.30% | 8.1 | 91.9 |
| Example 3 | 0.20% | 12.9 | 87.1 |
| Example 3 | 0.30% | 6.7 | 93.3 |

*Comparative

The above data show the optimal spray drift properties of the aqueous adjuvant concentrates of the invention.

The invention claimed is:

1. An aqueous adjuvant concentrate comprising from about 33 to about 40% by weight of ammonium sulfate, from about 1 to about 10% by weight of anionic esters of alkyl polyglycosides and from about 2 to about 10% by weight of hydroxypropyl guar or hydroxypropyl guar acetate;
wherein the aqueous adjuvant concentrate is pourable, does not include a suspending aid or water soluble organic solvent, and the hydroxypropyl guar or hydroxypropyl guar acetate is in dispersed form.

2. The aqueous adjuvant concentrate according of claim 1 wherein the anionic esters of alkyl polyglycosides are compounds represented by the formula (I) [R—O-(G)x]n-(D)y, where R is an aliphatic alkyl group, saturated or unsaturated, linear or branched, having from about 6 to about 20 atoms of carbon; G is a residue of a reducing saccharide, connected to R—O by means of an ethereal O-glycosidical bond; O is an oxygen atom; D is an acyl residue connected to an oxygen atom of the residue G, and derived from a bicarboxylic acid or a polycarboxylic acid having an aliphatic chain from about 2 to about 8 carbon atoms, linear or branched, saturated or unsaturated, not substituted or substituted with one or more hydroxyl groups or with a sulfonate group, and in which at least one carboxylic group is salified or in acid form; n is a number between 1 and m-1, where m is the number of carboxylic groups in the acid that originates D; x is a number from 1 to 10, representing the average degree of oligomerization of G; y is a number from 1 to 10 representing the medium degree of esterification.

3. The aqueous adjuvant concentrate of claim 2 wherein in formula (I) R is an aliphatic alkyl group, saturated or unsaturated, linear or branched, having from about 8 to about 16 carbon atoms, G is glucose, x is between about 1.0 and about 2.5, and D is the acyl residue of a carboxylic acid selected from the group consisting of citric acid, tartaric acid, maleic acid, malic acid and sulfosuccinic acid.

4. The aqueous adjuvant concentrate of claim 3 wherein the hydroxypropyl guar has a molar hydroxypropyl substitution of from about 0.1 to about 3.0, the hydroxypropyl guar acetate has molar hydroxypropyl substitution from about 0.1 to about 1.0 and contains an average of from about 0.001 to about 0.15 of acetate groups per anhydroglycosidic unit and the Brookfield RVT viscosity at 20° C., 20 rpm and 1% in water of the hydroxypropyl guar and the hydroxypropyl guar acetate is from about 500 to about 10,000 mPa·s.

5. The aqueous adjuvant concentrate of claim 1 wherein the hydroxypropyl guar is a glyoxalated hydroxypropyl guar, having molar substitution from about 0.1 to about 3.0 and Brookfield RVT viscosity at 20° C., 20 rpm, 1% in water of from about 1500 to about 3500 mPa·s.

6. The aqueous adjuvant concentrate of claim 4 wherein the hydroxypropyl guar is a glyoxalated hydroxypropyl guar, having molar substitution from about 0.1 to about 3.0 and Brookfield RVT viscosity at 20° C., 20 rpm, 1% in water is from about 1500 to about 3500 mPa·s.

7. The aqueous adjuvant concentrate of claim 1 prepared in the substantial absence of pinolene compounds.

8. A method for preparing an aqueous adjuvant concentrate of claim 1 comprising the steps of:
i) dissolving from about 15 to about 30% by weight, on the weight of the final concentrate, of ammonium sulfate in water;
ii) adding to the solution from about 1 to about 10% by weight, on the weight of the final concentrate, of anionic esters of alkyl polyglycosides;
iii) dispersing in the solution from about 2 to about 10% by weight, on the weight of the final concentrate, of hydroxypropyl guar or hydroxypropyl guar acetate; and
iiii) adding ammonium sulfate to the dispersion to reach an ammonium sulfate final concentration of from about 33 to about 40% by weight.

9. The method of claim 8 wherein the anionic esters of alkyl polyglycosides are compounds represented by the formula (I) [R—O-(G)x]n-(D)y, where R is an aliphatic alkyl group, saturated or unsaturated, linear or branched, having from about 6 to about 20 atoms of carbon; G is a residue of a reducing saccharide, connected to R—O by means of an ethereal O-glycosidical bond; O is an oxygen atom; D is an acyl residue connected to an oxygen atom of the residue G, and derived from a bicarboxylic acid or a polycarboxylic acid having an aliphatic chain from about 2 to about 8 carbon atoms, linear or branched, saturated or unsaturated, not substituted or substituted with one or more hydroxyl groups or with a sulfonate group, and in which at least one carboxylic group is salified or in acid form; n is a number between 1 and m-1, where m is the number of carboxylic groups in the acid that originates D; x is a number from 1 to 10, representing the average degree of oligomerization of G; y is a number from 1 to 10 representing the medium degree of esterification.

10. The method of claim 9 wherein in formula (I) R is an aliphatic alkyl group, saturated or unsaturated, linear or branched, having from about 8 to about 16 carbon atoms, G is glucose, x is between about 1.0 and about 2.5, and D is the acyl residue of a carboxylic acid selected from the group consisting of citric acid, tartaric acid, maleic acid, malic acid and sulfosuccinic acid.

11. The method of claim 10 wherein the hydroxypropyl guar has a molar hydroxypropyl substitution of from about 0.1 to about 3.0, the hydroxypropyl guar acetate has molar hydroxypropyl substitution from about 0.1 to about 1.0 and contains an average of from about 0.001 to about 0.15 of acetate groups per an hydroglycosidic unit and the Brookfield RVT viscosity at 20° C., 20 rpm and 1% in water of the hydroxypropyl guar and the hydroxypropyl guar acetate is from about 500 to about 10,000 mPa·s.

12. The method of claim 8 wherein the hydroxypropyl guar is a glyoxalated hydroxypropyl guar, having molar substitution from about 0.1 to about 3.0 and Brookfield RVT viscosity at 20° C., 20 rpm, 1% in water of from about 1500 to about 3500mPa·s.

13. The method of claim 11 wherein the hydroxypropyl guar is a glyoxalated hydroxypropyl guar, having molar substitution from about 0.1 to about 3.0 and Brookfield RVT viscosity at 20° C., 20 rpm, 1% in water is from about 1500 to about 3500mPa·s.

14. The method of claim 8 further comprising preparing the aqueous adjuvant concentrate of claim 1 in the substantial absence of pinolene compounds.

15. A sprayable herbicidal formulation comprising from about 0.01 to about 5% by weight at least one herbicide and the aqueous adjuvant concentrate of claim 1 in such an amount that the concentration of hydroxypropyl guar or hydroxypropyl guar acetate in the formulation is present at a concentration of from about 0.05 to about 0.4% by weight.

16. The sprayable herbicidal formulation of claim 15 wherein the sprayable herbicidal formulation is prepared in the substantial absence of pinolene compounds.

17. A sprayable herbicidal formulation of claim 15 wherein the herbicide is chosen from the group consisting of N-(phosphonomethyl) glycine and its salts.

18. A sprayable herbicidal formulation of claim 16 wherein the herbicide is chosen from the group consisting of N-(phosphonomethyl) glycine and its salts.

* * * * *